(12) United States Patent
Chen et al.

(10) Patent No.: US 9,448,325 B2
(45) Date of Patent: Sep. 20, 2016

(54) APPARATUS AND METHOD FOR RAY SCANNING IMAGING

(71) Applicants: Nuctech Company Limited, Beijing (CN); Tsinghua University, Beijing (CN)

(72) Inventors: Zhiqiang Chen, Beijing (CN); Li Zhang, Beijing (CN); Ziran Zhao, Beijing (CN); Yuxiang Xing, Beijing (CN); Jia Hao, Beijing (CN); Liang Li, Beijing (CN)

(73) Assignees: Nutech Company Limited, Beijing (CN); Tsinghua University, Beijing (CN)

( * ) Notice: Subject to any disclaimer, the term of this patent is extended or adjusted under 35 U.S.C. 154(b) by 114 days.

(21) Appl. No.: 14/129,655

(22) PCT Filed: Dec. 31, 2012

(86) PCT No.: PCT/CN2012/088079
§ 371 (c)(1),
(2) Date: Dec. 27, 2013

(87) PCT Pub. No.: WO2013/131402
PCT Pub. Date: Sep. 12, 2013

(65) Prior Publication Data
US 2014/0211917 A1 Jul. 31, 2014

(30) Foreign Application Priority Data
Mar. 9, 2012 (CN) .......................... 2012 1 0059992

(51) Int. Cl.
*G01V 5/00* (2006.01)
*G01N 23/04* (2006.01)
(Continued)

(52) U.S. Cl.
CPC ............. *G01V 5/0016* (2013.01); *A61B 6/032* (2013.01); *A61B 6/4007* (2013.01);
(Continued)

(58) Field of Classification Search
CPC ...... A61B 6/032; A61B 6/40; A61B 6/4007; A61B 6/4014; A61B 6/4275; G01N 23/046; G01V 5/0016; G01V 5/0041; G01V 5/005
USPC .............. 378/4, 5, 9, 10, 19, 57, 98.9, 98.11
See application file for complete search history.

(56) References Cited

U.S. PATENT DOCUMENTS 4,150,293 A 4/1979 Franke
4,709,382 A * 11/1987 Sones .............................. 378/62
(Continued)

FOREIGN PATENT DOCUMENTS

| CN | 101951837 A | 1/2011 |
|---|---|---|
| CN | 102551783 A | 7/2012 |

(Continued)

OTHER PUBLICATIONS

International Search Report and Written Opinion for PCT Application No. PCT/CN2012/088079, dated Mar. 28, 2013, 11 pages.
(Continued)

*Primary Examiner* — Allen C. Ho
(74) *Attorney, Agent, or Firm* — Westman, Champlin & Koehler, P.A.

(57) ABSTRACT

The present invention discloses apparatus and method for ray scanning imaging. The apparatus comprises a plurality of ray generators and a ray detection device. The plurality of ray generators are arranged uniformly along a circular arc and emit ray beams in sequence or simultaneously to an object to be inspected within a single scanning period. The ray detection device may be either in a multi-segmental semi-closed configuration composed of a plurality of linear arrays of ray detectors or in a circular arc configuration where a plurality of ray detectors arranged uniformly along a circular arc. During the inspection, the apparatus is advantageous in obtaining the complete ray projection values without rotation thereof, so as to effectively shorten the inspection time.

8 Claims, 6 Drawing Sheets

(51) Int. Cl.
    *A61B 6/03*         (2006.01)
    *A61B 6/00*         (2006.01)
    *G01T 1/29*         (2006.01)

(52) U.S. Cl.
    CPC .......... *A61B 6/4014* (2013.01); *A61B 6/4078* (2013.01); *A61B 6/4233* (2013.01); *A61B 6/4275* (2013.01); *G01N 23/046* (2013.01); *G01T 1/2985* (2013.01); *G01V 5/005* (2013.01)

(56) References Cited

U.S. PATENT DOCUMENTS

| | | | | |
|---|---|---|---|---|
| 4,792,900 | A * | 12/1988 | Sones et al. | 600/407 |
| 5,570,403 | A * | 10/1996 | Yamazaki et al. | 378/5 |
| 6,018,562 | A * | 1/2000 | Willson | 378/9 |
| 6,041,132 | A * | 3/2000 | Isaacs et al. | 382/100 |
| 6,236,709 | B1 * | 5/2001 | Perry et al. | 378/57 |
| 6,453,003 | B1 * | 9/2002 | Springer | G01N 23/06 378/51 |
| 6,580,778 | B2 * | 6/2003 | Meder | G01V 5/0041 378/57 |
| 6,597,759 | B2 * | 7/2003 | Mazess et al. | 378/53 |
| 6,597,760 | B2 * | 7/2003 | Beneke | G01V 5/0041 378/57 |
| 6,693,988 | B2 * | 2/2004 | Harding | 378/57 |
| 6,904,118 | B2 * | 6/2005 | Wu et al. | 378/5 |
| 6,987,833 | B2 * | 1/2006 | Du et al. | 378/98.9 |
| 7,020,241 | B2 * | 3/2006 | Beneke | G01V 5/0016 378/57 |
| 7,039,154 | B1 * | 5/2006 | Ellenbogen et al. | 378/19 |
| 7,082,182 | B2 * | 7/2006 | Zhou et al. | 378/10 |
| 7,103,137 | B2 * | 9/2006 | Seppi et al. | 378/9 |
| 7,106,825 | B2 * | 9/2006 | Gregerson | G06T 11/005 378/19 |
| 7,158,611 | B2 * | 1/2007 | Heismann et al. | 378/98.9 |
| 7,164,747 | B2 * | 1/2007 | Ellenbogen et al. | 378/19 |
| 7,192,031 | B2 * | 3/2007 | Dunham et al. | 378/122 |
| 7,215,737 | B2 * | 5/2007 | Li et al. | 378/57 |
| 7,233,644 | B1 | 6/2007 | Bendahan et al. | |
| 7,280,631 | B2 * | 10/2007 | De Man et al. | 378/10 |
| 7,319,737 | B2 * | 1/2008 | Singh | 378/57 |
| 7,327,903 | B2 * | 2/2008 | Riddell | G06T 11/005 382/154 |
| 7,400,701 | B1 * | 7/2008 | Cason | G01V 5/0025 378/57 |
| 7,428,292 | B2 * | 9/2008 | De Man et al. | 378/9 |
| 7,440,543 | B2 * | 10/2008 | Morton | 378/53 |
| 7,499,523 | B2 * | 3/2009 | Harding | G01N 23/20083 378/86 |
| 7,564,939 | B2 * | 7/2009 | Morton et al. | 378/9 |
| 7,606,348 | B2 * | 10/2009 | Foland | G01N 23/046 378/4 |
| 7,606,349 | B2 * | 10/2009 | Oreper | G01V 5/005 378/137 |
| 7,613,274 | B2 * | 11/2009 | Tkaczyk et al. | 378/5 |
| 7,616,731 | B2 * | 11/2009 | Pack et al. | 378/10 |
| 7,684,538 | B2 * | 3/2010 | Morton et al. | 378/10 |
| 7,706,499 | B2 * | 4/2010 | Pack et al. | 378/9 |
| 7,778,380 | B2 * | 8/2010 | Altman et al. | 378/4 |
| 7,831,012 | B2 * | 11/2010 | Foland | G01N 23/04 378/57 |
| 7,835,486 | B2 * | 11/2010 | Basu et al. | 378/9 |
| 7,864,917 | B2 * | 1/2011 | Ribbing et al. | 378/9 |
| 7,869,566 | B2 * | 1/2011 | Edic et al. | 378/57 |
| 7,885,372 | B2 * | 2/2011 | Edic et al. | 378/5 |
| 7,949,101 | B2 * | 5/2011 | Morton | 378/124 |
| 8,111,803 | B2 * | 2/2012 | Edic et al. | 378/5 |
| 8,160,206 | B2 * | 4/2012 | Wu et al. | 378/98.9 |
| 8,223,919 | B2 * | 7/2012 | Morton | G01N 23/046 378/57 |
| 8,243,874 | B2 * | 8/2012 | Carmi | 378/5 |
| 8,243,876 | B2 * | 8/2012 | Morton | 378/19 |
| 8,363,917 | B2 * | 1/2013 | Fan et al. | 382/131 |
| 8,391,439 | B2 * | 3/2013 | Levene et al. | 378/5 |
| 8,439,565 | B2 * | 5/2013 | Mastronardi et al. | 378/57 |
| 8,442,184 | B2 * | 5/2013 | Forthmann et al. | 378/5 |
| 8,472,583 | B2 * | 6/2013 | Star-Lack et al. | 378/57 |
| 8,491,188 | B2 * | 7/2013 | Vogtmeier et al. | 378/197 |
| 8,509,380 | B2 * | 8/2013 | Pelc | A61B 6/032 378/9 |
| 8,611,489 | B2 * | 12/2013 | Roessl | 378/5 |
| 8,699,657 | B2 * | 4/2014 | Baeumer et al. | 378/9 |
| 8,848,864 | B2 * | 9/2014 | Jeong et al. | 378/25 |
| 8,971,487 | B2 * | 3/2015 | Mastronardi et al. | 378/57 |
| 2004/0213378 | A1 | 10/2004 | Zhou et al. | |
| 2005/0111610 | A1 | 5/2005 | De Man et al. | |
| 2005/0175151 | A1 | 8/2005 | Dunham et al. | |
| 2007/0009081 | A1 | 1/2007 | Zhou et al. | |
| 2011/0002441 | A1 | 1/2011 | Vogtmeier et al. | |

FOREIGN PATENT DOCUMENTS

| | | |
|---|---|---|
| CN | 202562861 U | 11/2012 |
| JP | 2003190143 A | 7/2003 |
| JP | 2005534009 A | 11/2005 |
| JP | 2006524548 A | 11/2006 |
| KR | 10-2009-0015929 A | 2/2009 |
| WO | 2004010127 A1 | 1/2004 |
| WO | 2007/088497 A1 | 8/2007 |
| WO | 2010/103331 A1 | 9/2010 |
| WO | 2010/138574 A1 | 12/2010 |

OTHER PUBLICATIONS

G.Z. Yue et al., AIP: Applied Physics Letters, "Generation of continuous and pulsed diagnostic imaging x-ray radiation using a carbon-nanotube-based field-emission cathode", Applied Physics Letters 81, 355 (2002); doi: 10.1063/1.1492305, Jul. 8, 2002, 4 pages.
Extended European Search Report for European Patent Application No. 12870875.7-1559, dated Jun. 29, 2015, 8 pages.
Russian Office Action for Russian Patent Application No. 2014138823, issued on Mar. 18, 2015, 8 pages.
First Japanese Office Action for Japanese Patent Application No. 2014-502986, dated Aug. 5, 2014, 4 pages.
First Office Action for Korean Patent Application No. 10-2014-7027486, dated Feb. 3, 2016, 6 pages.
Communication pursuant to Article 94(3) EPC for European Patent Application No. 12 870 875.7-1559, dated May 17, 2016, 5 pages.

* cited by examiner

APPARATUS AND METHOD FOR RAY SCANNING IMAGING

CROSS-REFERENCE TO RELATED APPLICATIONS

This application is a Section 371 National Stage Application of International Application No. PCT/CN2012/088079, filed 31 Dec. 2012 and published as WO 2013/131402 A1 on 12 Sep. 2013, which claims priority from and the benefit of Chinese Patent Application No. 201210059992.6, titled "APPARATUS AND METHOD FOR RAY SCANNING IMAGING", filed on Mar. 9, 2012, the disclosure of which is incorporated herein by reference in its entirety.

BACKGROUND OF THE INVENTION

1. Technical Field

The present invention relates to a radiation imaging field, and in particular, to apparatus and method for ray scanning imaging.

2. Brief Description of Related Art

Nowadays radiation imaging apparatus has been widely utilized in public places and important departments, such as airports, stations, customs, subways, harbors, etc., for performing security inspection of goods such as luggage or cargo in a high efficient and stable manner as all the countries in the world pay more attention on security inspection.

Radiation imaging apparatus is generally made in accordance with principles of exponential ray attenuation. That is, scanning of the object to be inspected is carried out by the ray beams emitted from the radiation source. The ray beams pass through the object to be inspected, and are received by the ray collection device. Three-dimensional images are composed or reconstructed and displayed based on ray detection values received by the ray collection device.

FIG. 1 shows a structural diagram of a prior art radiation imaging apparatus.

The radiation imaging apparatus comprises a gantry 13, a ray source 11 connected to the gantry 13, a detection arrangement 12 placed, opposite to the ray source 11, on the gantry 13, and a delivery device 14 for delivery of the object to be inspected. During the inspection operation, the gantry 13 brings the ray source 11 and the detection arrangement 12 to rotate so as to achieve ray projection values for different rays under different angles and to obtain tomography images for the object to be inspected by means of reconstruction.

The applicant has made in-depth study on the prior art radiation imaging apparatus and found that, the prior art radiation imaging apparatus has low detection efficiency because rotations of the ray source 11 and the detection arrangement 12 are brought by the gantry 13 with a limited rotational speed. Accordingly, the prior art radiation imaging apparatus is hard to satisfy the existing requirements, for example, the requirement of a clearance rate of 0.5 m/s, for civil aviation goods.

SUMMARY

In order to solve the issue of low detection efficiency existing in the prior art radiation imaging apparatus, the inventors of the present invention has proposed a new technical solution.

Accordingly, it is an object of the present invention to provide an apparatus for ray scanning imaging, which effectively shortens inspection time for an object to be inspected.

Accordingly, it is another object of the present invention to provide a method for ray scanning imaging, which achieves and processes ray collection values to obtain an image for an object to be inspected, by means of such apparatus for ray scanning imaging.

According to a first aspect of the present invention, an apparatus for ray scanning imaging is provided. The apparatus comprises a plurality of ray generators distributed uniformly along a circular arc, and a ray detection device. The plurality of ray generators emits ray beams in sequence to an object to be inspected within a single scanning period, to complete scanning for a single slice. The ray detection device is adapted for collecting ray projection values of the ray beams emitted by the plurality of ray generators.

Preferably, a central angle of the circular arc on which the plurality of ray generators are arranged is at least $\pi+2\gamma$, where $2\gamma$ is a fan angle of a fan ray beam emitted by the ray generators.

Preferably, the ray generators each comprise at least one ray emission unit.

Alternatively, the ray beams are fan ray beams or are ray beam units composed of a plurality of straight line-shaped ray beams in parallel with each other.

Alternatively, the ray detection device is a circular arc array of ray detectors in which a plurality of ray detectors are distributed uniformly along a circular arc.

Preferably, the ray detection device comprises a plurality of linear arrays of ray detectors. Each of the plurality of linear arrays of ray detectors is composed of a plurality of ray detectors arranged along a straight line. The plurality of linear arrays of ray detectors adjoin end to end in a same plane in sequence except that two of the plurality of linear arrays of ray detectors at both ends thereof do not adjoin each other, so as to form a semi-closed frame.

Alternatively, the number of the plurality of linear arrays of ray detectors may be greater than 3. In such case, the plurality of linear arrays of ray detectors are arranged in a manner such that an angle between two adjacent linear arrays of ray detectors is greater than $\pi/2$ and the plurality of linear arrays of ray detectors are capable of detecting the ray beams emitted by all the ray generators.

Preferably, the number of the plurality of linear arrays of ray detectors may be 3. In such case, the three linear arrays of ray detectors are arranged in a manner such that the linear arrays of ray detectors on both sides are all perpendicular to the middle linear array of ray detectors and the three linear arrays of ray detectors are capable of detecting the ray beams emitted by all the ray generators.

Preferably, the plane where the plurality of linear arrays of ray detectors are placed and a plane where the plurality of ray generators are placed being in parallel with the former are perpendicular to a movement direction of the object to be inspected.

Preferably, this apparatus further comprises an imaging unit that achieves an image for the object to be inspected by processing ray detection values collected by the ray detection device.

Preferably, in one embodiment, for the ray detection device composed of the plurality of linear arrays of ray detectors, the plurality of ray detectors corresponding to at least one of the ray generators are not arranged in a straight line that is perpendicular to a central axis of the ray beams emitted by the at least one of the ray generators. For every one of the at least one of the ray generators, the imaging unit arranges a linear array of equidistant virtual detectors comprising a plurality of virtual detectors arranged along a straight line and distributed equidistantly. Distances between all of the at least one of the ray generators and the corresponding linear arrays of equidistant virtual detectors are equal to one another. The imaging unit, in accordance with connection lines between the ray generator and the plurality of ray detectors, can determine the plurality of ray detectors corresponding to the plurality of virtual detectors, and achieves ray detection values of the plurality of virtual detectors on the basis of those of the plurality of ray detectors. An equidistant fan beam projection value can be composed of the ray detection values of all the linear arrays of equidistant virtual detectors.

In another embodiment, for the ray detection device composed of the plurality of circular arc-shaped arrays of ray detectors, when the ray beams are fan ray beams, equidistant fan beam projection values are composed of the ray detection values achieved by the ray detection device; when the ray beams are units of ray beam composed of a plurality of straight line-shaped ray beams in parallel with each other, parallel beam projection values are composed of the ray detection values achieved by the ray detection device.

Preferably, the plurality of ray detectors may be dual-layer dual-energy energy detectors. The imaging unit may achieve an image for the object to be inspected, by, with a filtered back projection algorithm, dual-energy reconstructing dual-energy decomposition coefficients of different basis materials achieved by dual-energy decomposing the equidistant fan beam projection values or the parallel beam projection values.

Preferably, this apparatus may further comprise a database adapted for storing atomic numbers and electron densities of suspicious items therein. The imaging unit may determine whether the object to be inspected is suspicious item or not, by comparing distributions of atomic number and electron density of the object to be inspected that is achieved in the dual-energy reconstruction with those of suspicious items in the database.

According to the first aspect of the present invention, another apparatus for ray scanning imaging is also provided. The apparatus comprises a plurality of ray generators distributed uniformly along a circular arc and a ray detection device. The plurality of ray generators emitting ray beams simultaneously to an object to be inspected within a single scanning period, to complete scanning for a single slice. The ray detection device is adapted for collecting ray projection values of the ray beams emitted by the plurality of ray generators.

Preferably, a central angle of the circular arc on which the plurality of ray generators are arranged is at least π.

Preferably, the ray generators each may comprise a plurality of ray emission units, and ray beams emitted from the plurality of ray emission units are straight line-shaped beams in parallel with each other; and the ray detection device may comprise a plurality of ray detectors, and the plurality of ray detectors corresponding to the whole ray emission units are not overlapped with each other.

Preferably, the plurality of ray detectors may be distributed uniformly along a circular arc such that the plurality of ray detectors and the ray emission units are arranged in a one-to-one relationship. Parallel beam projection values may be composed of ray detection values achieved by all the ray detectors.

Preferably, a plane where the plurality of ray detectors are placed and a plane where the plurality of ray generators are placed being in parallel with the former are perpendicular to a movement direction of the object to be inspected.

Preferably, this apparatus may further comprise an imaging unit that achieves an image for the object to be inspected by processing ray detection values collected by the ray detection device.

Preferably, the plurality of ray detectors may be dual-layer dual-energy energy detectors. The imaging unit may achieve an image for the object to be inspected, by, with a filtered back projection algorithm, dual-energy reconstructing dual-energy decomposition coefficients of different basis materials achieved by dual-energy decomposing the parallel beam projection values.

Preferably, this apparatus may further comprise a database adapted for storing atomic numbers and electron densities of suspicious items therein. The imaging unit determines whether the object to be inspected is suspicious item or not, by comparing distributions of atomic number and electron density of the object to be inspected that is achieved in the dual-energy reconstruction with those of suspicious items in the database.

According to a second aspect of the present invention, a method for ray scanning imaging is provided. This method comprises the steps of:

performing, by any one of the above two apparatuses, a ray scanning on the object to be inspected to achieve ray detection values.

When the former apparatus is adopted, for a ray detection device composed of the plurality of linear arrays of ray detectors, arranging a linear array of equidistant virtual detectors for every one of at least one of the ray generators which corresponds to the plurality of ray detectors that are not arranged in a straight line perpendicular to a central axis of the ray beams emitted by the at least one of the ray generators. The linear array of equidistant virtual detectors may comprise a plurality of virtual detectors arranged along a straight line and distributed equidistantly. Distances between all of the at least one of the ray generators and the corresponding linear arrays of equidistant virtual detectors are equal to one another. In accordance with connection lines between the ray generators and the plurality of ray detectors, the plurality of ray detectors corresponding to the virtual detectors, respectively, are then determined and, ray detection values of the virtual detectors are achieved on the basis of those of the ray detectors. An equidistant fan beam projection value is composed of the ray detection values of the whole linear arrays of equidistant virtual detectors.

For the ray detection device composed of the plurality of ray detectors distributed along a circular arc, equidistant fan beam projection values or parallel beam projection values are composed of the ray detection values achieved by the ray detection device.

When the latter apparatus is adopted, for the ray detection device composed of the plurality of ray detectors distributed along the circular arc, parallel beam projection values are composed of the ray detection values achieved by the ray detection device.

Preferably, this method may comprise the steps of: achieving dual-energy decomposition coefficients of different basis materials by dual-energy decomposing the equidistant fan beam projection values or the parallel beam projection values; and, achieving an image for the object to be inspected, by, with a filtered back projection algorithm, dual-energy reconstructing dual-energy decomposition coefficients of different basis materials.

Preferably, this method may further comprise the steps of: achieving distributions of atomic number and electron density of the object to be inspected; and comparing distributions of the atomic number and the electron density of the object to be inspected with those of suspicious items stored in the database, so as to determine whether the object to be inspected is suspicious item or not.

The apparatus according to the present invention comprises a plurality of ray generators and a matching ray detection device. The plurality of ray generators may be distributed uniformly along a circular arc. The ray detection device may be either in a multi-segmental semi-closed frame composed of a plurality of linear arrays of ray detectors or in oval ray detection arrays. By adoption of such configuration, rotatable gantry mechanism in a conventional apparatus for ray scanning imaging is omitted. During a practical inspection operation, a plurality of ray generators emit ray beams in sequence to an object to be inspected and the ray detection device takes charge of collection of the ray projection values, so as to complete scanning for a single slice. During the whole inspection operation, the complete ray projection values can be obtained rapidly without rotations of the plurality of ray generators and the ray detection device, such that the inspection time is shortened effectively.

BRIEF DESCRIPTION OF THE DRAWINGS

The accompanying drawings which constitute a part of the description will illustrate the embodiments of the present invention, and, together with the others of the description, will set forth principles of the present invention.

These and/or other aspects and advantages of the invention will become more apparent and more readily appreciated from the following description of the embodiments, taken in conjunction with the accompanying drawings of which.

DETAILED DESCRIPTION OF EXEMPLARY EMBODIMENTS

Reference will now be made in detail to exemplary embodiments of the present specification, taken in conjunction with the accompanying drawings. It should be noted that the scope of the present invention will in no way be limited to components, steps and the relative arrangement thereof, numerical expressions and values, etc., set forth in these embodiments, unless otherwise specified.

Meanwhile, it should be understood that, these figures in the accompanying drawings may not be drawn to scale, helping to description of the present invention.

The following description is presented only by way of illustrations and possesses no limitations on applications and uses of the present invention.

Known technologies, methods and apparatuses for those skilled in the art may be not discussed in detail, excluding, in some suitable situations, those seen as parts of the present specification.

In these exemplary embodiments described and illustrated below, any specific values are explained only by way of representation and no limitations. Accordingly, different values may be adopted in alternative examples of these exemplary embodiments.

It should be noted that like reference numbers and characters may have been used throughout these figures to denote like parts. Accordingly, once definition of one reference number/character is made in one figure, no further explanations are required in its succeeding figures.

Figure 1:
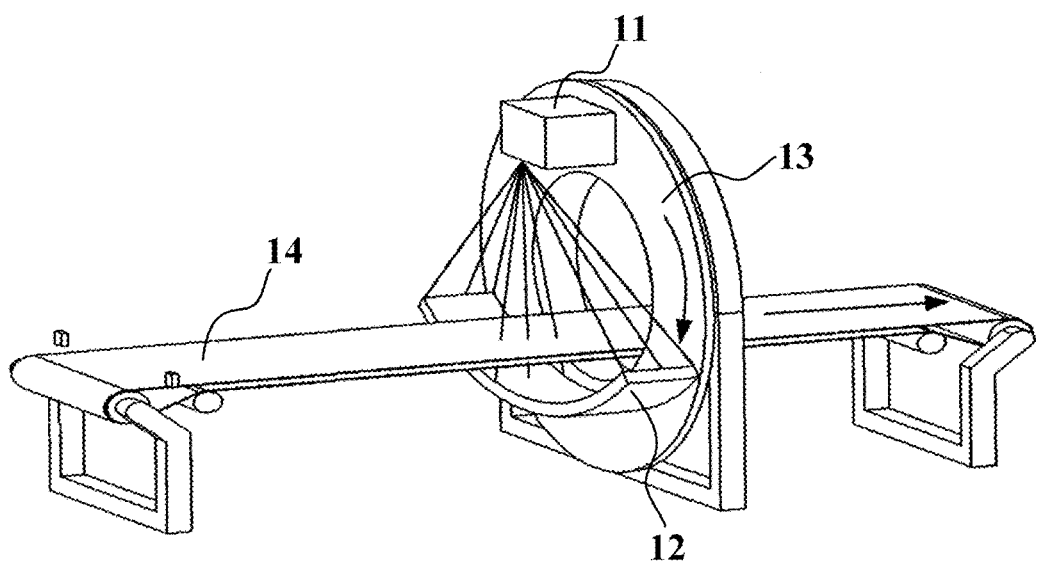
FIG. 1 is a structural diagram of a prior art apparatus for ray scanning imaging.
Figure 2:
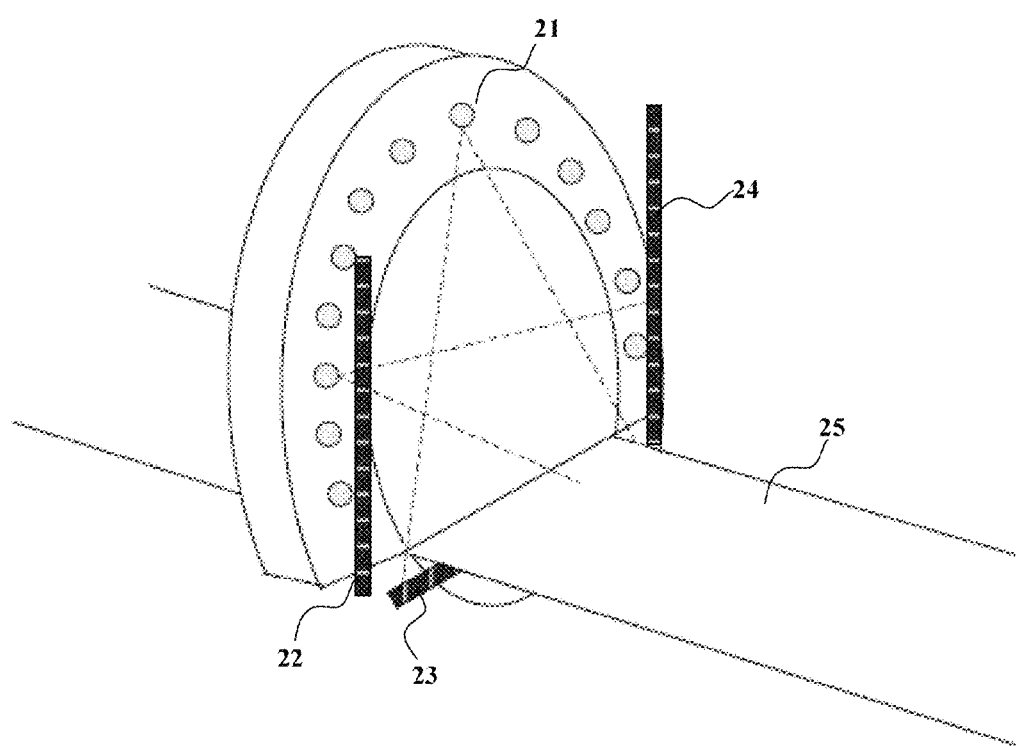
FIG. 2 is a structural diagram of an embodiment of an apparatus for ray scanning imaging according to the present invention.

FIG. 2 shows a structural diagram of an embodiment of an apparatus for ray scanning imaging according to the present invention.

The apparatus for ray scanning imaging may comprise a ray detection device and a plurality of ray generators 21.

When an object to be inspected is brought to the scanning region of the apparatus, the plurality of ray generators 21 can emit the ray beams in sequence to the object to be inspected, to perform scanning for a single slice of the object to be inspected.

After passing through the object to be inspected, all the ray beams are collected by the ray detection device.

The ray detection device may be arranged in any suitable configuration, for example, either a multi-segmental semi-closed configuration or a circular arc configuration. In this embodiment, the description is made by taking a ray detection device in the multi-segmental semi-closed adjoining configuration composed of a plurality of linear arrays of ray detectors as an example.

The plurality of ray generators 21 may be distributed along a specific shape such that the object to be inspected passes through the space formed by the specific shape. For example, the plurality of ray generators 21 may be disposed along a rectangular frame, a polygonal frame, or any other geometrical frame, so that the object to be inspected passes through the inner space formed by the frame. In this embodiment, the plurality of ray generators 21 are distributed uniformly along a circular arc. The central angle of the circular arc is at least $\pi+2\gamma$, where $2\gamma$ is a complete fan angle of a fan ray beam.

In this embodiment, a plurality of linear arrays 22, 23, and 24 of ray detectors in a segmented manner may be adjoined. Specifically, a linear array 22 of ray detectors, a linear array 23 of ray detectors, and a linear array 24 of ray detectors adjoin end to end in a same plane in sequence except that the linear array 22 of ray detectors and the linear array 24 of ray detectors do not adjoin each other, so as to form an inverted doorframe-shaped semi-closed frame. Each of the linear arrays 22, 23, and 24 of ray detectors may include a plurality of ray detectors arranged along a straight line.

A delivery device 25 may be used to carry the object to be inspected to pass through the scanning region. Within a single scanning period, the plurality of ray generators 21 emit the ray beams in sequence to the object to be inspected, so as to complete scan for a single slice. After passing through the objected to be inspected, the ray beams are collected by the linear arrays 22, 23, and 24 of ray detectors. By processing the collected ray values, a reconstructed image of the object to be inspected can be obtained.

A plane where the plurality of linear arrays 22, 23, and 24 of ray detectors are placed and a plane where the plurality of ray generators 21 are placed should be two different ones.

Preferably, the two planes may be in parallel with each other and both perpendicular to a movement direction of the object to be inspected. Thus, crosstalk and radiation blind zone among the plurality of ray detectors may be avoided.

Next, the conditions of data completeness required for accurate reconstruction by use of the fan ray beams will be explained. The conditions of data completeness includes, firstly, a condition of angle completeness, that is, a ray radiation angle for the object to be inspected is at least π+2γ, where 2γ is a complete fan angle of the fan ray beam; and, secondly, a condition of ensuring that ray values collected by the linear arrays 22, 23, and 24 of ray detectors are not truncated under all scanning angles, i.e., a condition of ensuring that all the ray beams emitted by the plurality of ray generators 21 can be detected effectively by the linear arrays 22, 23, and 24 of ray detectors under all the scanning angles.

In this embodiment, the ray beam emitted by each of the plurality of ray generators 21 can be a fan beam with a fan angle of 2γ. Of course, the ray beam can have other form, instead of a fan form. For example, in accordance with practical requirement, each ray generator 21 is provided with one or more ray emission openings each emitting a straight line-shaped ray beam. Thus, the ray emission openings of each ray generator 21 can emit a unit of parallel ray beams.

X-ray generator, or other types of ray generators, may be used as the ray generator 21. Preferably, in this embodiment, carbon nanotube X-ray generator may be used as the ray generator 21. Compared with those conventional X-ray machines, the carbon nanotube X-ray generator has the advantages, such as ray emission generation without under high temperature, quicker switch on and off, and less volume. Ray imaging speed is efficiently enhanced when multiple angle radiation of the carbon nanotube X-ray generator on the object to be inspected is performed. For details of the carbon nanotube X-ray generator, refers to the following documents, G. Z. Yue, Q. Qiu, B. Gao, et al. Generation of continuous and pulsed diagnostic imaging x-ray radiation using a carbon-nanotube-based field-emission cathode. Appl. Phys. Lett. 81, 355(2002); doi:10.1063/1.1492305, and the detailed description is omitted herein.

The central angle of the circular arc on which the plurality of ray generators 21 is arranged is π+2γ in the embodiment. That is, the plurality of ray generators 21 performs the scanning on the object to be inspected within an angle range of π+2γ. In other words, configuration of the plurality of ray generators 21 according to the present invention fulfills the requirement for the angle completeness condition of the conditions of data completeness.

As to the second requirement of the conditions of data completeness, the plurality of ray generators 21 are disposed in an annular semi-closed configuration and the linear array 22 of ray detectors, the linear array 23 of ray detectors, and the linear array 24 of ray detectors form a corresponding frame-shaped semi-closed configuration, so that all the ray beams generated from each of the plurality of ray generators 21 can be detected effectively by the linear arrays 22, 23, and 24 of ray detectors. Thus, such configuration fulfills the second requirement of the conditions of data completeness.

A dual-layer dual-energy energy detector may be used as the ray detector. Of course, any types of detectors may also be used as the ray detector, for example, monoenergy detector, multiple energy detector, or, true-dual energy detector.

The adopted dual-layer dual-energy energy detector comprises two layers of crystals and a filter between the two layers of crystals. The filter may be a copper filter. A first layer of crystals is used to achieve low energy ray values while a second layer of crystals is used to achieve reshaped high energy ray values. This type dual-layer dual-energy energy detector has advantages such as high quality, lower price, and ease to be widely used.

It should be noted that the number of the linear arrays of ray detectors is not limited to three, as shown in FIG. 2. For example, four or more linear arrays of ray detectors may be adopted to collect the ray values. In such case, the angle between every two adjacent linear arrays of ray detectors should be greater than π/2.

The number, angles and lengths of the linear arrays of ray detectors can also be adjusted in accordance with factors, such as volume, shape, etc., of the object to be inspected, although the used linear arrays of ray detectors above all should fulfill the conditions of data completeness.

As adopting a multi-segmental semi-closed frame configuration, the plurality of linear arrays of ray detectors according to the present invention not only collects completely ray projection values, but also possesses higher performance-to-price ratio compared with the conventional circular arc array of detectors. Specifically, provided that there is same number of the detectors, the plurality of linear arrays of ray detectors according to the present invention may form a greater inner space and allow passage of the object to be inspected with greater volume, and, provided that there is same size of the inner spaces, such structural configuration according to the present invention adopts less detectors and reduces the cost.

In addition, a ray detection device of other configurations, instead of the multi-segmental semi-closed configuration shown in FIG. 2, may be adopted. For example, circular arc array of ray detectors, in which a plurality of ray detectors distributed uniformly along a circular arc is included, may be adopted.

The apparatus for ray scanning imaging may further comprise an imaging unit, which may achieve a tomography image for the object to be inspected by processing ray detection values collected by the linear arrays of ray detectors.

Of course, ray detection values collected by the linear arrays 22, 23, and 24 of ray detectors may also be sent to, via a date delivery system, and numerically processed by a main control and data processing terminal.

Before introducing detailed description of the data processing, the structural requirements of the reconstruction method on the ray detectors under fan ray beams will be explained.

Standard fan beam weighted filtered back projection (FBP) reconstruction method is only applicable to two kinds of detector arrangements, one is an equiangular configuration, that is, the multiple detectors are arranged in a circular arc manner and the angles between beams corresponding to every detectors are equivalent to each other, and the other is an equidistant configuration, that is, the multiple detectors are arranged in a straight line-shaped and the distances from one detector to its adjacent detector are equivalent to each other and central axis of ray beam emitted by every ray generator 21 is perpendicular to a straight line where multiple detectors are arranged. In case that unit of ray beams in a straight line is used, a method which is similar to the above-mentioned reconstruction method may be adopted and will not be described here.

In this embodiment, arrangement of detectors corresponding to some of the plurality of ray generators 21 does not fulfill the equidistant configuration requirement for the above-mentioned reconstruction method, because of adoptions of the annular configuration of the plurality of ray generators 21 and the multi-segmental semi-closed configuration of the linear arrays 22, 23, and 24 of ray detectors. Specifically, the ray detectors corresponding to some of the plurality of ray generators 21 are not arranged in a straight line that is perpendicular to the central axis of ray beam emitted by such ray generators. The followings are explanations and illustrations of such arrangement with reference to FIG. 3 and FIG. 4.

Figure 3:
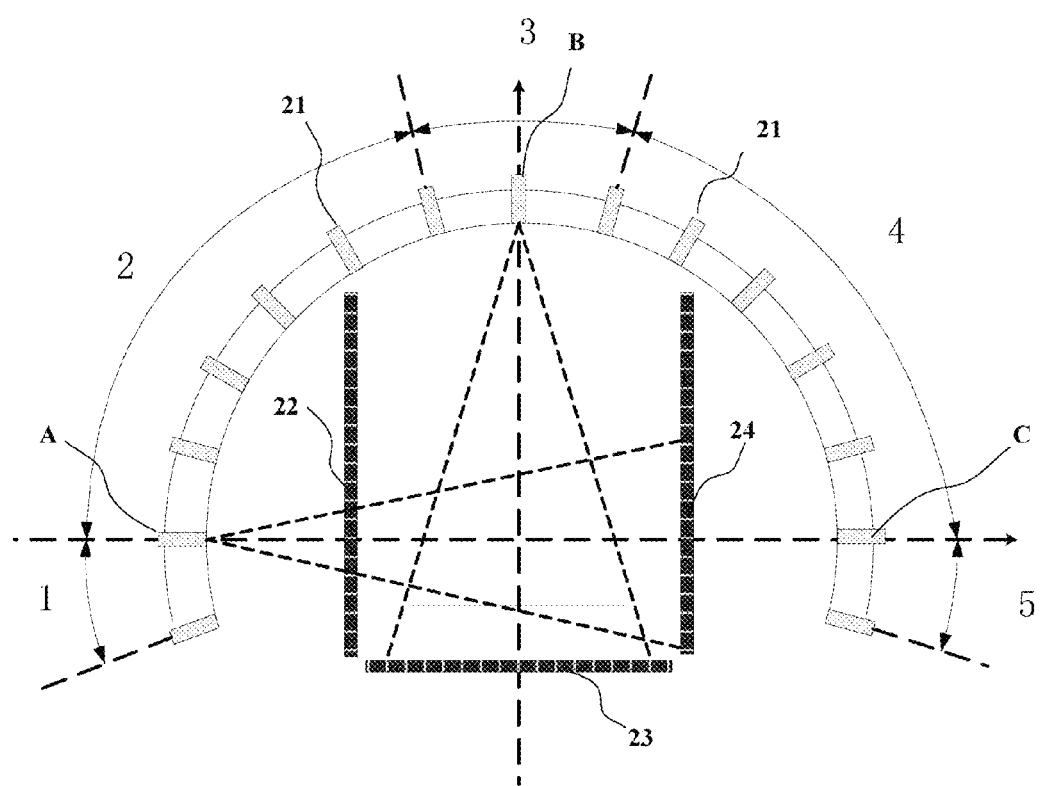
FIG. 3 is a diagram showing a positional relationship between ray generators and linear arrays of ray detectors in the embodiment of the apparatus for ray scanning imaging according to the present invention.

FIG. 3 shows the diagram of a positional relationship between ray generators and linear arrays of ray detectors in the embodiment.

As shown in FIG. 3, all the ray detectors corresponding to a ray generator A are located on the linear array 24 of ray detectors, and a straight line where the ray detectors are arranged is perpendicular to central axis of the ray beams emitted by the ray generator A, and distances from one detector to its adjacent detector are equivalent to each other. That is to say, to the ray generator A, the ray detectors are arranged in the equidistant configuration required for standard fan beam FBP reconstruction method.

Similarly, there are some ray detectors corresponding to the ray generators B and C, respectively. Whatever, all these ray detectors corresponding to the rest of the ray generators are not arranged in the equidistant configuration required for standard fan beam FBP reconstruction method.

In order to further explain and illustrate such configuration, provided that the circular arc where the plurality of ray generators 21 is arranged is divided into five regions 1-5, in which, the ray beams emitted from the ray generators 21 in region 1 are collected only by the linear array 24 of ray detectors at the right side, the ray beams emitted from the ray generators 21 in region 2 are collected both by the linear array 24 of ray detectors at the right side and the linear array 23 of ray detectors at the bottom, the ray beams emitted from the ray generators 21 in region 3 are collected only by the linear array 23 of ray detectors at the bottom, the ray beams emitted from the ray generators 21 in region 4 are collected both by the linear array 22 of ray detectors at the left side and the linear array 23 of ray detectors at the bottom, and, the ray beams emitted from the ray generators 21 in region 5 are collected only by the linear array 22 of ray detectors at the left side.

Taking the ray generators 21 in the region 1 and their corresponding ray detectors as an example, the situation where the collected ray values are non-equidistant ray collected values is explained hereinafter.

Figure 4A:
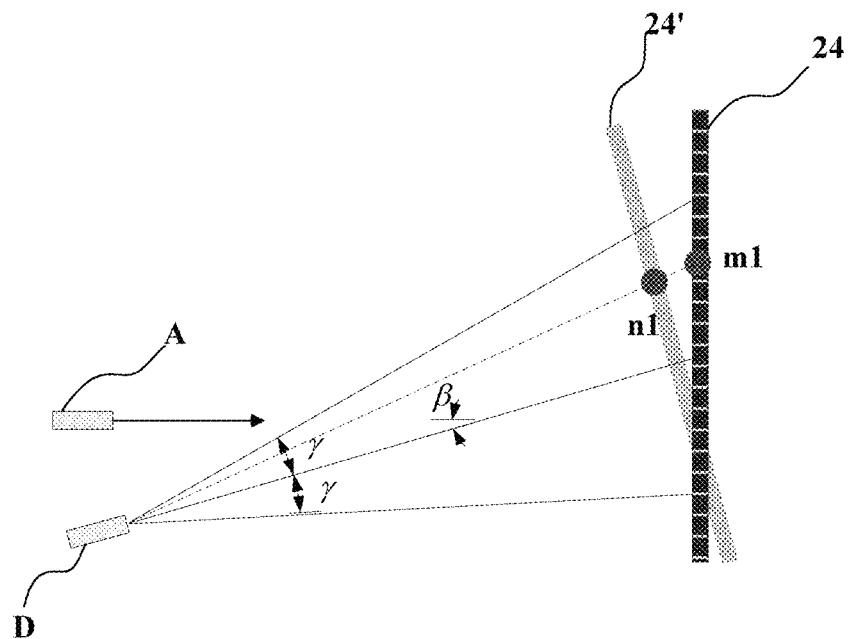
FIGS. 4A and 4B are diagrams respectively showing a positional relationship among ray generators, ray detectors and virtual ray detectors, in different regions.

FIG. 4A is a diagram of a positional relationship among ray generator, arrays of ray detectors and virtual ray detectors in the region 1.

As shown in FIG. 4A, the linear array 24 of real ray detectors is perpendicular to central axis of the ray beams emitted by the ray generator A but is not perpendicular to central axis of the ray beams emitted by the ray generator D. Accordingly, for the ray generator D, the ray values of the ray beams collected by the linear array 24 of ray detectors are not the equidistant ray collecting values. In this embodiment, β is a sampling angle corresponding to the projection data, and 2γ is a maximum fan angle for fan ray beam.

In order to solve this problem, the imaging unit may employ a linear array 24' of equidistant virtual ray detectors corresponding to the ray generator D, for the ray generator D.

The linear array 24' of equidistant virtual detectors may comprise a plurality of virtual detectors arranged along a straight line and distributed equidistantly. The linear array 24' of equidistant virtual detectors is perpendicular to central axis of the ray beams emitted by the ray generator D.

Then the imaging unit, in accordance with connection lines between the ray generator D and the linear array 24 of ray detectors, determines a ray detector m1 corresponding to the virtual detector n1, and achieves ray detection value of the virtual detector n1 on the basis of that of the ray detector m1. Other virtual detectors on the linear array 24' of equidistant virtual ray detectors may be achieved in the above manner.

Figure 4B:
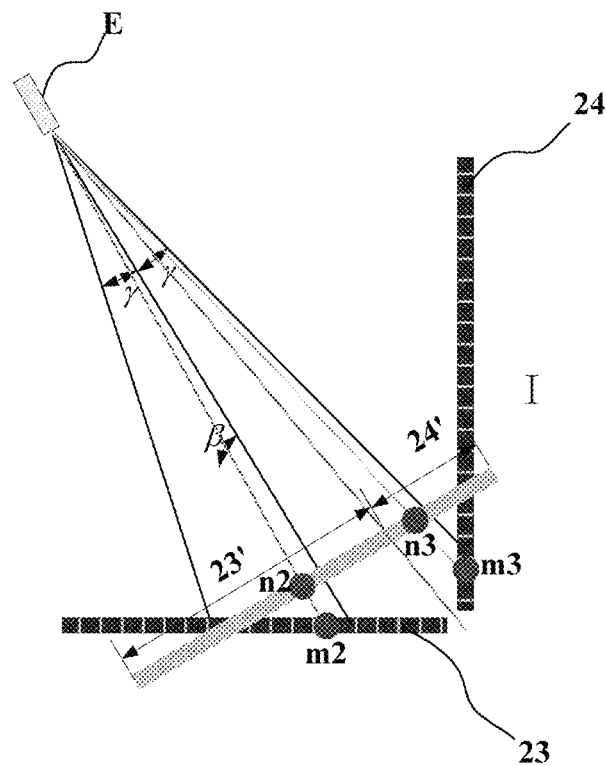

FIG. 4B is a diagram of a positional relationship among ray generator E, arrays of ray detectors and virtual ray detectors in the region 2.

In FIG. 4B, the ray beams emitted by the ray generator E in the region 2 are collected commonly by linear array 24 of ray detectors at the right side and the linear array 23 of ray detectors at the bottom, and, the ray values of the ray beams collected are not the equidistant ray collecting values.

Similar to those in FIG. 4A, in order to achieve the equidistant ray collecting values, the imaging unit provides a linear array 23' of virtual ray detectors and a linear array 24' of virtual ray detectors both combined and arranged along a straight line.

Then, the imaging unit, in accordance with connection lines between the ray generator E and the linear array 23 of ray detectors and the linear array 24 of ray detectors, determines a ray detector m2 corresponding to the virtual detector n2 and a ray detector m3 corresponding to the virtual detector n3, and may achieve ray detection values of the virtual detectors n2 and n3 on the basis of those of the ray detectors m2 and m3.

Other linear arrays of ray detectors corresponding to the ray generators in the region 3 to the region 5 may be achieved in a similar manner, and their descriptions are omitted for clarity.

It should be noted that, in the linear array of equidistant virtual detectors achieved by the above-mentioned method, some virtual ray detectors may be non-equidistant, or, one real ray detector corresponds to a plurality of virtual ray detectors. In the cases, a post process may be done after a final image is obtained, or, positions of the plurality of virtual ray detectors may be adjusted in a suitable method so as to fulfill the equidistant requirements among the virtual ray detectors.

Distances between every ray generator and its corresponding linear array of equidistant virtual detectors are also equal to each other. For example, such distance may be set as the one between the ray generator A and the linear array 24 of ray detectors.

In this way, an equidistant fan beam projection value is composed of the ray detection values of all the linear arrays 22, 23 and 24 of equidistant virtual detectors and the linear arrays of detectors corresponding to the ray generators A, B, and C.

Similarly, in a case that the ray detection device composed of circular arc-shaped arrays of ray detectors is adopted, an equidistant fan beam projection value is composed of the ray detection values achieved by this device if the ray beams are the fan ones; and, a parallel beam projection value is composed of the ray detection values achieved by this device if the ray beams are the unit of ray beams composed of the straight line-shaped ray beams in parallel with each other. The descriptions are omitted for clarity.

Provided that the ray detectors are dual-layer dual-energy energy detectors, the imaging unit can achieve dual-energy decomposition coefficients of different basis materials by dual-energy decomposing the equidistant fan beam projection values. Then, the image for the object to be inspected can be achieved by, with a filtered back projection algorithm, dual-energy reconstructing dual-energy decomposition coefficients of different basis materials.

The apparatus may further comprise a database which may store atomic numbers and electron densities of suspicious items therein. The imaging unit determines whether the object to be inspected is suspicious item or not, by comparing distributions of atomic number and electron density of the object to be inspected that is achieved in the dual-energy reconstruction with those of suspicious items in the database.

Accordingly, the apparatus according to the present invention can achieve the scanning imaging of the object to be inspected, without a gantry mechanism. Within a single scanning period, the plurality of ray generators emit the ray beams in sequence to the object to be inspected, and the linear arrays of ray detectors are used for collection of the ray projection values, so as to complete scan for a single slice. During the whole inspection operation, this apparatus can obtain rapidly the complete ray projection values without rotations thereof, such that the inspection time is shortened effectively.

Further, the apparatus according to the present invention, without the gantry mechanism, has the advantages such as less volume of the whole apparatus, less cost, and higher quality of the achieved image for the object to be inspected due to avoiding non-distinct imaging issues caused during the rotation.

Still further, the technical solution according to the present invention adopts linear arrays of dual-layer dual-energy detectors together with scanning and reconstruction of short scan CT, which reduces effectively influence of shielding of luggage and goods on the safety inspection operation.

Figure 5:
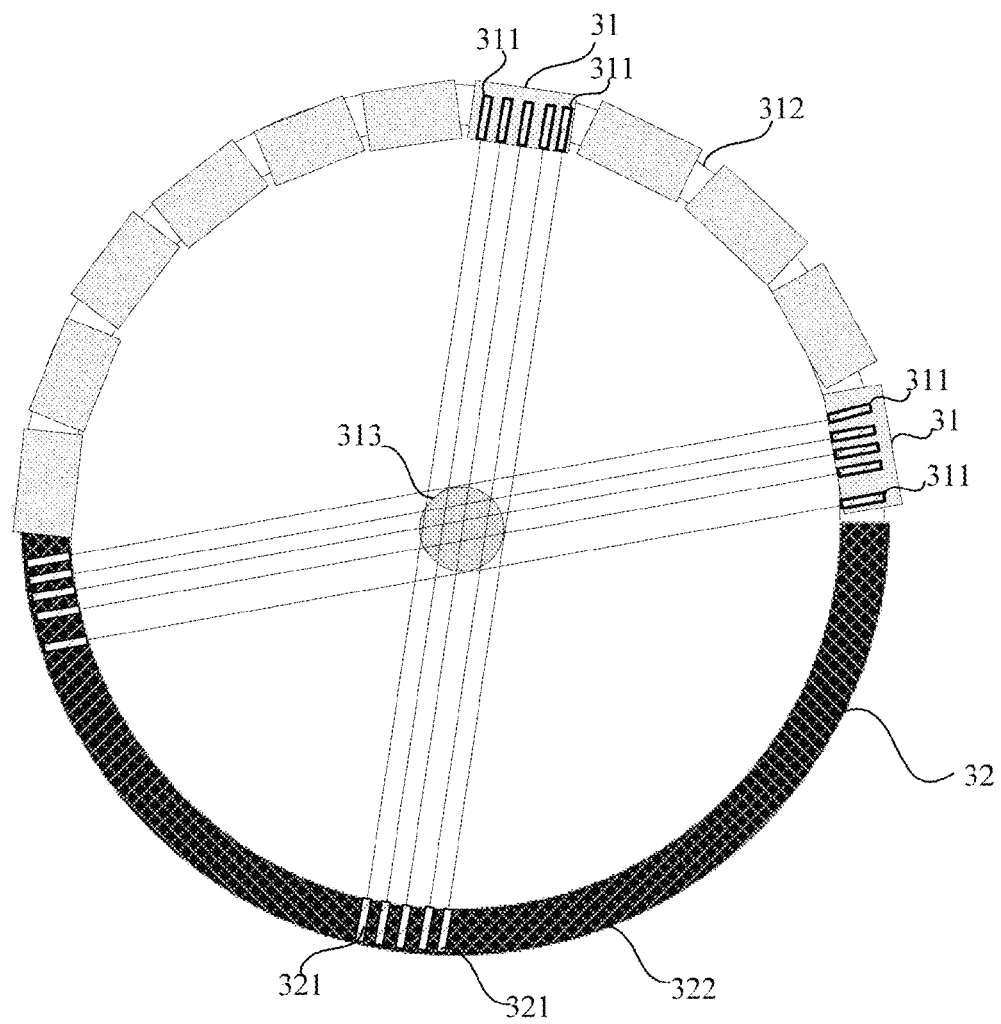
FIG. 5 is a structural diagram of another embodiment of an apparatus for ray scanning imaging according to the present invention.

FIG. 5 shows a structural diagram of another embodiment of an apparatus for ray scanning imaging according to the present invention.

The apparatus comprises a ray detection device 32 and a plurality of ray generators 31.

The plurality of ray generators 31 are distributed uniformly along a circular arc 312. The central angle of the circular arc 312 is at least 180°. The plurality of ray generators 31 may emit ray beams simultaneously to an object to be inspected within a single scanning period. The ray beams are detected by the ray detection device 32 after passing through the object to be inspected.

Every ray generator 31 can be provided with a plurality of ray emission units 311. In this embodiment, each ray generator 31 is provided with five ray emission units 311. The five ray emission units 311 may emit parallel straight line-shaped ray beams simultaneously, to form a unit of ray beams. As shown in the figure, overlapping regions among the plurality of units of ray beams serve as the scanning region 313 (Field of View, FOV).

Correspondingly, the ray detection device 32 comprises a plurality of ray detectors 321. The plurality of ray detectors 321 are distributed uniformly along a circular arc 322. A radius of the circular arc 322 is equal to that of the circular arc 312 while a central angle of the circular arc 322 is a straight angle. Accordingly, the ray emission units 311 on the plurality of ray generators 31 corresponds one by one to the plurality of ray detectors 321 on the ray detection device 32. In this way, the ray beams emitted by all the ray emission units 311 are not overlapped with each other when impinging on the ray detection device 32. When an object to be inspected passes through the scanning region 313, a tomography scan is performed on this object to be inspected. The parallel ray beam projection value is composed of ray detection values achieved by this device.

A plane where the ray detection device 32 is placed and a plane where the plurality of ray generators 31 are placed should be two different ones. Preferably, the two planes are in parallel with each other and are both perpendicular to a movement direction of the object to be inspected.

The imaging unit, then, processes the ray detection values collected by the ray detection device 32, so as to obtain image for the object to be inspected.

It is not needed, in this embodiment, to rearrange the achieved ray detection values since distances between all the ray emission units 311 and corresponding ray detectors 321 are equal to one another. The dual-energy decomposition coefficients of different basis materials may be achieved by directly dual-energy decomposing the parallel beam projection values, and, an image for the object to be inspected may be achieved by, with a filtered back projection algorithm, dual-energy reconstructing dual-energy decomposition coefficients of different basis materials.

Further, the imaging unit may also achieve atomic number and electron density of the object to be inspected in the dual-energy reconstruction and determine whether the object to be inspected is suspicious item or not, by comparing the atomic number and electron density of the object to be inspected with those of suspicious items in the database.

Related reconstruction method is omitted as it is similar to that of the former embodiment.

It should be noted that the apparatus according to the present invention may adopt any structures and configurations with which it is ensured that the ray beams emitted by all the ray emission units 311 would not be overlapped with each other when impinging on the ray detection device 32 and is not limited to those structures and configurations shown in the drawings. That is, situations that the ray beams emitted by two or more ray emission units 311 are collected simultaneously by one ray detector 321 should be avoided. For example, central angle of the circular arc 322 may be larger than that of the circular arc 312 along which the plurality of ray generators 31 are arranged, radius of the circular arc 322 may be larger than that of the circular arc 312, and, the number of the ray detectors 321 may be more than that of the ray emission units 311.

Still further, the ray detection device 32 may be in any other configuration, instead of the circular arc configuration. For example, the ray detection device 32 may be arranged in a three sectional or multi-sectional manner as in the above embodiments so long as the ray beams emitted by all the ray emission units 311 would not be overlapped with each other when impinging on the ray detection device 32. Correspondingly, first of all, virtual detectors corresponding to the ray detectors 321 should be achieved, and detection values of the virtual detectors are achieved based on those of the ray detectors 321. Then, the image for the object to be inspected is obtained by performing a reconstruction by the ray detection values of the virtual detectors.

The plurality of ray emission units 311 of the apparatus can emit ray beams simultaneously towards the object to be inspected, so that the inspection time for the object to be inspected is shortened effectively, so as to greatly shorten its clearance time.

Figure 6:
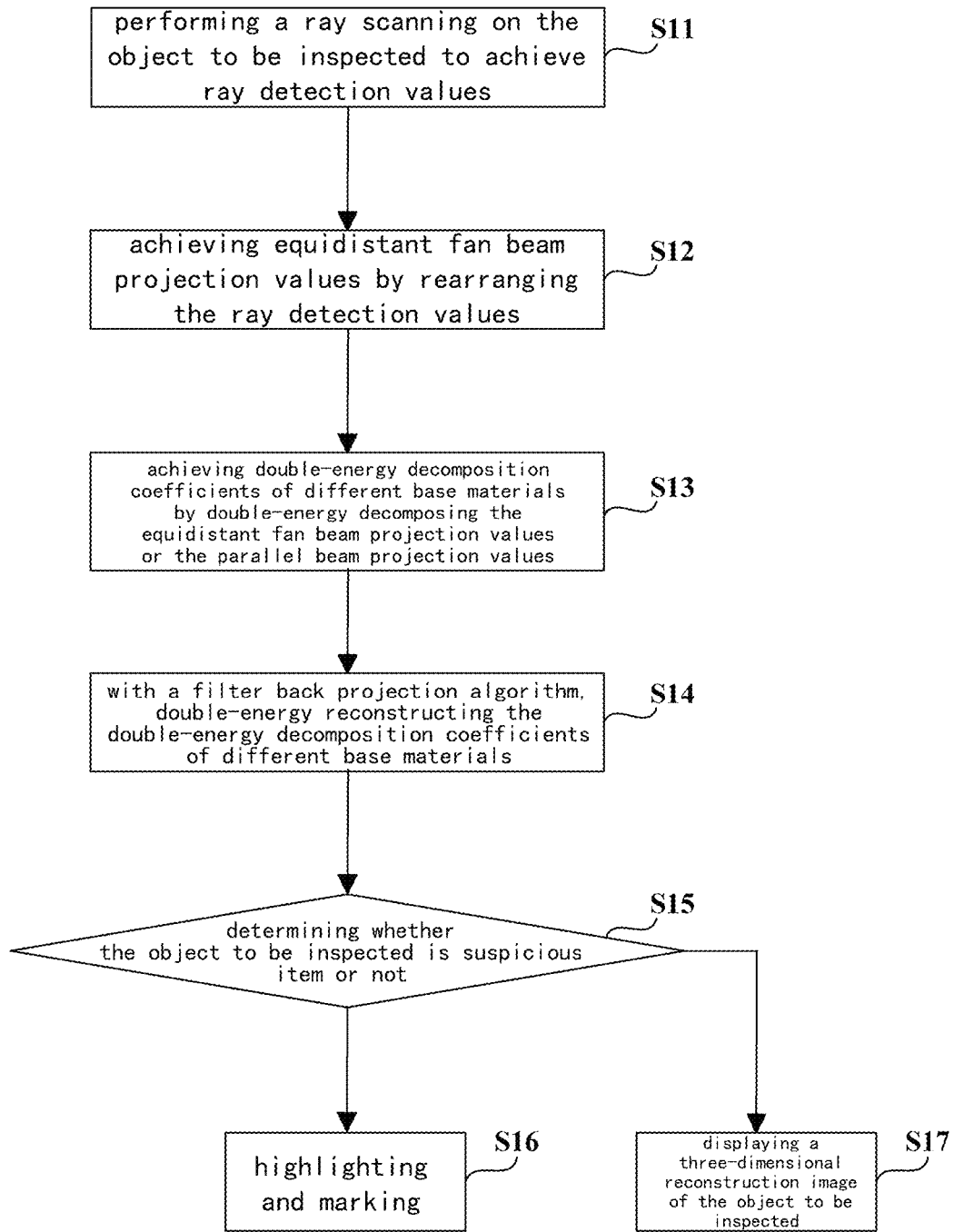
FIG. 6 is a flow diagram of an embodiment of a method for processing ray detection values according to the present invention.

FIG. 6 is a flow diagram of an embodiment of a method for processing ray detection values according to the present invention.

At step S11, a ray scanning on the object to be inspected is performed to achieve ray detection values.

The scanning and detection may be performed by using any one of the apparatuses for ray scanning imaging according to the present invention. Specifically, a plurality of ray generators may emit ray beams in sequence to an object to be inspected, to complete scan for a single slice. And, a ray detection device may collect the ray beams and achieve ray detection values.

At step S12, the ray detection values are rearranged to achieve equidistant fan beam projection values.

Preferably, before this step S12, pretreatment and correction of the ray detection values, which includes the operations like elimination of air value and local negative logarithm calculation, uniformity correction, determination and removal of detector' bad track, etc., may be performed.

The followings relates to the description made by taking a ray detection device formed of a plurality of linear arrays of ray detectors, and a fan ray beam as an example. Suitable adjustments may be made to the ray detection devices of any other configurations and the ray beams of any other form, with reference to this method.

In this case, linear array of equidistant virtual detectors may be provided for each of the ray generators. The linear array of equidistant virtual detectors may comprise multiple virtual detectors arranged along a straight line and distributed equidistantly.

Distances between all of the ray generators and the corresponding arrays of equidistant virtual detectors should be equal to one another.

Then, in accordance with connection lines between the ray generators and the virtual detectors, the ray detectors corresponding to the virtual detectors are determined respectively, and, ray detection values of the virtual detectors are achieved on the basis of those of the ray detectors.

An equidistant fan beam projection value is composed of the ray detection values of all the linear arrays of equidistant virtual detectors and the linear arrays of detectors corresponding to the ray generators A, B, and C.

In this embodiment, the method of processing the ray detection values may further comprises the following steps.

A step S13 of achieving dual-energy decomposition coefficients of different basis materials by dual-energy decomposing the equidistant fan beam projection values is included.

The dual-energy decomposition coefficients A1 and A2 of different basis materials can be achieved by dual-energy decomposing the equidistant fan beam projection values, with a basis material decomposition method.

A step S14 of achieving image for the object to be inspected, by, with a filtered back projection algorithm, dual-energy reconstructing dual-energy decomposition coefficients of different basis materials is included.

In particular, the reconstructed dual-energy reconstruction coefficients a1 and a2 can be achieved respectively by performing a CT reconstruction of the dual-energy decomposition coefficients A1 and A2 in accordance with a short scan and weighted reconstruction method, and, the weighted coefficient can be achieved by the following formula:

$$\omega(\gamma, \beta) = \begin{cases} \sin^2\left(\frac{\pi}{4}\frac{\beta}{\gamma_m - \gamma}\right), & \beta \in [0, 2\gamma - 2\gamma_m] \\ 1, & \beta \in [2\gamma - 2\gamma_m, \pi - 2\gamma] \\ \sin^2\left(\frac{\pi}{4}\frac{\pi + 2\gamma_m - \beta}{\gamma_m + \gamma}\right), & \beta \in [\pi - 2\gamma, \pi + 2\gamma_m] \end{cases}$$

in which, $\beta$ is a sampling angle corresponding to the projection data, and $2\gamma$ is a maximum fan angle for fan ray beam. Of course, the used weighted coefficient can be achieved by utilizing any other suitable methods, instead of the above formula.

Preferably, this method may still further comprise the following steps.

A step S15 of determining whether the object to be inspected is suspicious item or not is included.

In this step, in order to achieve atomic number and electron density of the object to be inspected, the dual-energy reconstruction coefficients a1 and a2 may be substituted into the following two formulas (1) and (2), $$Z = \left[\frac{a_1\rho_{e1}Z_1^{3.5} + a_2\rho_{e2}Z_2^{3.5}}{a_1\rho_{e1} + a_2\rho_{e2}}\right]^{1/3.5} \quad (1)$$

$$\rho_e = a_1\rho_{e1} + a_2\rho_{e2}, \quad (2)$$

in which $Z_1$ and $Z_2$ are the atomic number of two basis materials, respectively, and, $\rho_{e1}$ and $\rho_{e2}$ are the electron density values of two basis materials, respectively.

Then, distribution values of the atomic number and electron density of the object to be inspected are compared with those of suspicious items, so as to determine whether the object to be inspected is suspicious item or not. Distributions of atomic numbers and electron densities of suspicious items can be stored in the database or other devices.

When it is determined that suspicious item(s) is included in the object to be inspected, a step S16 of displaying a category to which the suspicious item(s) belongs and marking a region where the suspicious item(s) is, for human inspection, is performed.

When it is determined that no suspicious item(s) is included in the object to be inspected, a step S17 of allowing the object to be inspected to pass through the inspection of this slice and performing a scanning on the next slice, and displaying a three-dimensional reconstruction image after the object to be inspected passes through the inspection of all slices, is performed.

Using this method, these dangerous suspicious items, such as combustible goods, explosive goods, narcotic drugs, etc., can be recognized quickly and accurately.

The apparatus and method for ray scanning imaging according to the present invention have been described and illustrated in detail, although some details belonging to well-known knowledge in the art have been omitted in order for emphasizing on the inventive concept of the present invention. Those skilled in the art will understand how to implement these technical solutions disclosed herein in accordance with the above description.

Although certain exemplary embodiments of the present invention have been shown and described, it will be appreciated by those skilled in the art that changes may be made in these exemplary embodiments without departing from the principles and spirit of the present invention, the scope of which is defined in the appended claims and their equivalents.

What is claimed is:

1. An apparatus for ray scanning imaging, the apparatus comprising:
    a plurality of ray generators distributed uniformly along a circular arc, said plurality of ray generators emitting ray beams in sequence to an object to be inspected within a single scanning period, to complete scan for a single slice; and
    a ray detection device adapted for collecting ray projection values of the ray beams emitted by said plurality of ray generators;
    wherein said ray detection device comprises a plurality of linear arrays of ray detectors, each of said plurality of linear arrays of ray detectors comprises a plurality of ray detectors arranged along a straight line, wherein said plurality of linear arrays of ray detectors adjoin end to end in a same plane in sequence except that two of the plurality of linear arrays of ray detectors at both ends thereof do not adjoin each other, so as to form a semi-closed frame; and
    wherein the plane where said plurality of linear arrays of ray detectors are placed and a plane where said plurality of ray generators are placed being in parallel with the plane where said plurality of linear arrays of ray detectors are placed are perpendicular to a movement direction of the object to be inspected.

2. The apparatus of claim 1, wherein a central angle of the circular arc on which said plurality of ray generators are arranged is at least $\pi+2\gamma$, where $2\gamma$ is a fan angle of a fan ray beam emitted by each of the plurality of ray generators;
    wherein each of the plurality of ray generators comprises at least one ray emission unit; and
    wherein said ray beams are fan ray beam units composed of a plurality of straight line-shaped ray beams in parallel with each other.

3. The apparatus of claim 1, wherein the plurality of linear arrays of ray detectors comprise more than three linear arrays of ray detectors, said more than three linear arrays of ray detectors are arranged in a manner such that an angle between two adjacent linear arrays of ray detectors is greater than $\pi/2$ and said more than three linear arrays of ray detectors are capable of detecting the ray beams emitted by all of said plurality of ray generators.

4. The apparatus of claim 1, wherein the plurality of linear arrays of ray detectors comprise only three linear arrays of ray detectors, said three linear arrays of ray detectors are arranged in a manner such that the three linear arrays of ray detectors on both sides are all perpendicular to the middle linear array of ray detectors and said three linear arrays of ray detectors can detect the ray beams emitted by all of said plurality of ray generators.

5. The apparatus of claim 1, wherein, the plurality of linear arrays of ray detectors corresponding to at least one of the plurality of ray generators are not arranged in a straight line that is perpendicular to a central axis of the ray beams emitted by the at least one of the plurality of ray generators;
    wherein, for every one of said at least one of the plurality of ray generators, an imaging unit adopts a linear array of equidistant virtual detectors comprising a plurality of virtual detectors arranged along a straight line and distributed equidistantly, distances between all of said at least one of the plurality of ray generators and the corresponding linear array of equidistant virtual detectors are equal to one another;
    wherein, said imaging unit, in accordance with connection lines between said plurality of ray generators and said plurality of linear arrays of ray detectors, determines the ray detectors corresponding to the virtual detectors, and achieves ray projection values of the virtual detectors on the basis of those of the ray detectors; and
    wherein, an equidistant fan beam projection value comprises the ray projection values of the whole linear array of equidistant virtual detectors.

6. The apparatus of claim 5, wherein said ray detectors are dual-layer dual-energy energy detectors;
    wherein said imaging unit achieves an image for the object to be inspected, by, with a filtered back projection algorithm, dual-energy reconstructing dual-energy decomposition coefficients of different basis materials achieved by dual-energy decomposing the equidistant fan beam projection values or the parallel beam projection values; and
    the apparatus further comprising a database adapted for storing atomic numbers and electron densities of suspicious items therein;
    wherein said imaging unit determines whether the object to be inspected is suspicious item or not, by comparing distributions of atomic number and electron density of the object to be inspected that is achieved in said dual-energy reconstruction with those of suspicious items in the database.

7. A method for ray scanning imaging, the method comprising the steps of:
    performing, by the apparatus according to claim 1, a ray scanning on the object to be inspected to achieve ray projection values;
    arranging a linear array of equidistant virtual detectors for every one of at least one of the plurality of ray generators which corresponds to ray detectors that are not arranged in a straight line perpendicular to a central axis of the ray beams emitted by the at least one of the plurality of ray generators, the linear array of equidistant virtual detectors comprising a plurality of virtual detectors arranged along a straight line and distributed equidistantly, distances between all of said at least one of the plurality of ray generators and the corresponding linear arrays of equidistant virtual detectors are equal to one another;
    in accordance with connection lines between said plurality of ray generators and said ray detectors, determining the ray detectors corresponding to the virtual detectors, and, achieving ray projection values of the virtual detectors on the basis of those of the ray detectors;
    wherein, an equidistant fan beam projection value comprises the ray projection values of the whole linear array of equidistant virtual detectors.

8. The method of claim 7, further comprising the steps of:
    achieving dual-energy decomposition coefficients of different basis materials by dual-energy decomposing the equidistant fan beam projection values or the parallel beam projection values; and
    achieving an image for the object to be inspected, by, with a filtered back projection algorithm, dual-energy reconstructing the dual-energy decomposition coefficients of different basis materials;
    achieving distributions of atomic number and electron density of the object to be inspected; and
    comparing distributions of the atomic number and the electron density of the object to be inspected with those of suspicious items stored in the database, so as to determine whether the object to be inspected is a suspicious item or not.

* * * * *